United States Patent
Biswas et al.

(10) Patent No.: US 9,056,816 B2
(45) Date of Patent: Jun. 16, 2015

(54) PROCESS FOR THE PREPARATION OF ALISKIREN

(71) Applicant: Jubilant Life Sciences Limited, Noida, Uttar Pradesh (IN)

(72) Inventors: Sujay Biswas, Uttar Pradesh (IN); Sankareswaran Srimurugan, Uttar Pradesh (IN); Anjul Kumar, Uttar Pradesh (IN); Atulya Kumar Panda, Uttar Pradesh (IN); Danish Jamshad, Uttar Pradesh (IN); Mukesh Masand, Uttar Pradesh (IN); Bidyut Biswas, Uttar Pradesh (IN); Vikas Bansal, Uttar Pradesh (IN); Ashish Kumar Gupta, Uttar Pradesh (IN); Dharam Vir, Uttar Pradesh (IN)

(73) Assignee: JUBILANT LIFE SCIENCES LIMITED, Noida, Uttar Pradesh (IN)

( * ) Notice: Subject to any disclaimer, the term of this patent is extended or adjusted under 35 U.S.C. 154(b) by 0 days.

(21) Appl. No.: 14/354,524

(22) PCT Filed: Oct. 19, 2012

(86) PCT No.: PCT/IB2012/055737
§ 371 (c)(1),
(2) Date: Apr. 25, 2014

(87) PCT Pub. No.: WO2013/061224
PCT Pub. Date: May 2, 2013

(65) Prior Publication Data
US 2014/0256963 A1    Sep. 11, 2014

(30) Foreign Application Priority Data

Oct. 25, 2011    (IN) .......................... 3046/DEL/2011

(51) Int. Cl.
*C07C 231/10* (2006.01)
*C07C 231/02* (2006.01)
*C07D 307/33* (2006.01)
*C07D 307/20* (2006.01)

(52) U.S. Cl.
CPC ............. *C07C 231/10* (2013.01); *C07C 231/02* (2013.01); *C07D 307/33* (2013.01); *C07D 307/20* (2013.01)

(58) Field of Classification Search
CPC ...................................... C07C 231/10
USPC ................... 549/320, 321; 564/157
See application file for complete search history.

(56) References Cited

U.S. PATENT DOCUMENTS

| 5,559,111 A | 9/1996 | Göschke et al. |
| 2009/0076062 A1 | 3/2009 | Maibaum et al. |

FOREIGN PATENT DOCUMENTS

WO    WO 2011/051853 A1    5/2011

*Primary Examiner* — Taofiq A Solola
(74) *Attorney, Agent, or Firm* — Knobbe, Martens, Olsen & Bear, LLP

(57) ABSTRACT

The present invention provides a novel process and novel intermediates useful in the synthesis of pharmaceutically active compounds, especially renin inhibitors, such as Aliskiren, or a salt thereof, preferably Aliskiren hemifumarate.

38 Claims, No Drawings

PROCESS FOR THE PREPARATION OF ALISKIREN

FIELD OF THE INVENTION

The invention relates to a novel process for the preparation of Aliskiren and pharmaceutically acceptable salts thereof, preferably Aliskiren hemifumarate.

BACKGROUND OF THE INVENTION

Aliskiren hemifumarate (Formula I) [CAS Registry Number: 173334-58-2], having the chemical name: (2S,4S,5S, 7S)—N-(2-carbamoyl-2-methylpropyl)-5-amino-4-hydroxy-2,7-diisopropyl-8-[4-methoxy-3-(3-methoxypropoxy)phenyl]octanamide hemifumarate [$C_{30}H_{53}N_3O_6 \cdot 0.5\ C_4H_4O_4$] and is depicted structurally as below:

Formula I

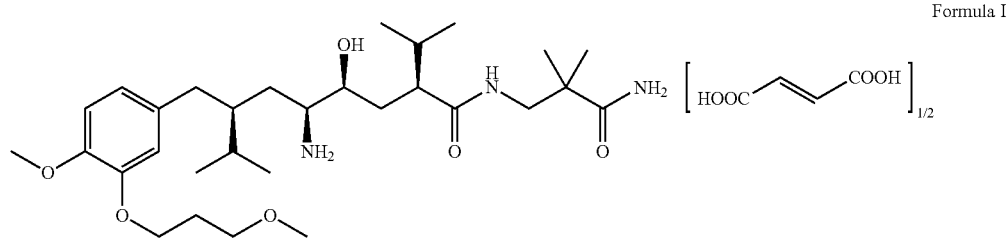

Aliskiren Hemifumarate

Aliskiren as renin inhibitor is generally known in the art. It is useful for the treatment of hypertension and its hemifumarate salt is commercially available under the trade names Tekturna® and Rasilez®.

Synthesis of Aliskiren and its related compounds are referred in U.S. Pat. No. 5,559,111, while pharmacological actions, pharmacokinetics and clinical studies of Aliskiren and its related compounds are referred to in Lindsay, K. B. et. al., J. Org. Chem., Vol. 71, pp 4766-4777 (2006) and in Drugs of the Future, Vol. 26, No. 12, pp 1139-1148 (2001).

As Aliskiren comprises 4 chiral centers, the synthesis of the diastereomerically and enantiomerically pure compound is quite challenging. Therefore, synthetic routes that allow more convenient synthesis of this complex molecule are welcome.

The main drawback in the product patent route (U.S. Pat. No. 5,559,111) is the deoxygenation of benzylic hydroxy (or as acyloxy) by hydrogenolysis using palladium catalyst which results in the formation of complex mixture of the products e.g. pyrrolidine derivative (derived from the reduction of azide followed by cyclization) as a major product and desired deoxygenated product along with only reduced product. The similar results were also observed even after opening the lactone ring. This problem has also been encountered during deoxygenation of benzylic hydroxy (or as acyloxy) even after protecting the azide nitrogen as carbamate to provide alkoxy carbonyl protected pyrrolidine as an exclusive product (also reported in literature). The incomplete reaction, use of excess metal catalyst, longer reaction time and purification of intermediates by column chromatography leads to poor yield of the final product and in turn it makes the process industrially unacceptable.

U.S. Pat. No. 6,683,206 refers to the process for the preparation of intermediate of Aliskiren hemifumarate, wherein deoxygenation of benzylic hydroxyl group is carried out by conversion of said hydroxyl group into the good leaving group, which is further removed by formation of conjugated double bond. Such deoxygenation methodology demands subsequent catalytic asymmetric hydrogenation, which requires expensive metal catalyst such as ruthenium, rhodium and iridium.

The major drawback of the process described in U.S. Pat. No. 6,800,769 is that all intermediates are reported as an oily mass, no intermediate is isolable as solid material. Purification of those intermediates is only possible by column chromatography, which is slow, tedious, lengthy and not industrially feasible. It is not desirable to perform column chromatography at all the intermediate stages and under such circumstances, impurities are being carried forward till the final API i.e. Aliskiren hemifumarate. Purification at the final stage to remove the various impurities affects the yield and in turn significantly increases the cost of API.

The drawbacks of the above mentioned prior art processes for the preparation of Aliskiren and its hemifumarate salt are low yield, accompanied with a number of side reactions, use of excess/expensive metal catalyst, longer reaction time and significant amount of various impurities.

Nevertheless, there still remains a need for industrial friendly, economical and efficient manufacturing process for the preparation of Aliskiren hemifumarate that is free from above mentioned drawbacks and achieves high yield and high degree of purity in environmental friendly condition.

The problem has been solved by the applicant by providing novel process and novel intermediates allowing a convenient and efficient synthesis of Aliskiren and pharmaceutically acceptable salts thereof, preferably Aliskiren hemifumarate.

OBJECT OF THE INVENTION

It is a principal object of the present invention to improve upon limitations in the prior arts by providing a novel process for the preparation of Aliskiren and pharmaceutically acceptable salts thereof, preferably Aliskiren hemifumarate.

It is another object of the present invention to provide a commercially viable, economical and environment friendly process for preparing Aliskiren and pharmaceutically acceptable salts thereof, preferably Aliskiren hemifumarate, in high yield and high purity.

It is still another object of the present invention to provide a novel process for the preparation of Aliskiren and pharmaceutically acceptable salts thereof, preferably Aliskiren hemifumarate, wherein the process is operationally simple and industrially feasible.

It is still another object of the present invention to provide a novel process for the preparation of Aliskiren and pharmaceutically acceptable salts thereof, preferably Aliskiren hemifumarate, via novel intermediates, wherein the process involves deoxygenation by ionic hydrogenation of Schiff's base, which is derived from azide compound by catalytic hydrogenolysis.

It is still another object of the present invention to provide a novel process for the preparation of Aliskiren and pharmaceutically acceptable salts thereof, preferably Aliskiren hemifumarate, wherein the process involves the reduction of azide compound, via novel intermediate, subsequently protecting the amino group, followed by coupling and deprotection.

It is still another object of the present invention to provide a novel process for the preparation of Aliskiren and pharmaceutically acceptable salts thereof, preferably Aliskiren hemifumarate, wherein the process involves the reduction of azide compound, via novel intermediate, and in-situ protection of the amino group, followed by coupling and deprotection.

It is still another object of the present invention to provide Aliskiren and its hemifumarate salt substantially free from these novel intermediates i.e. (compound of Formula VII-imine, Formula VIIA-imine and Formula VIIA-Int).

It is still another object of the present invention to provide Aliskiren and its hemifumarate salt substantially free from dimeric impurity i.e. compound of Formula VIIA-amine-dimer.

SUMMARY OF THE INVENTION

According to one aspect of the present invention there is provided a novel and cost effective process for the manufacture of Aliskiren hemifumarate of Formula I, as shown in Scheme 1.

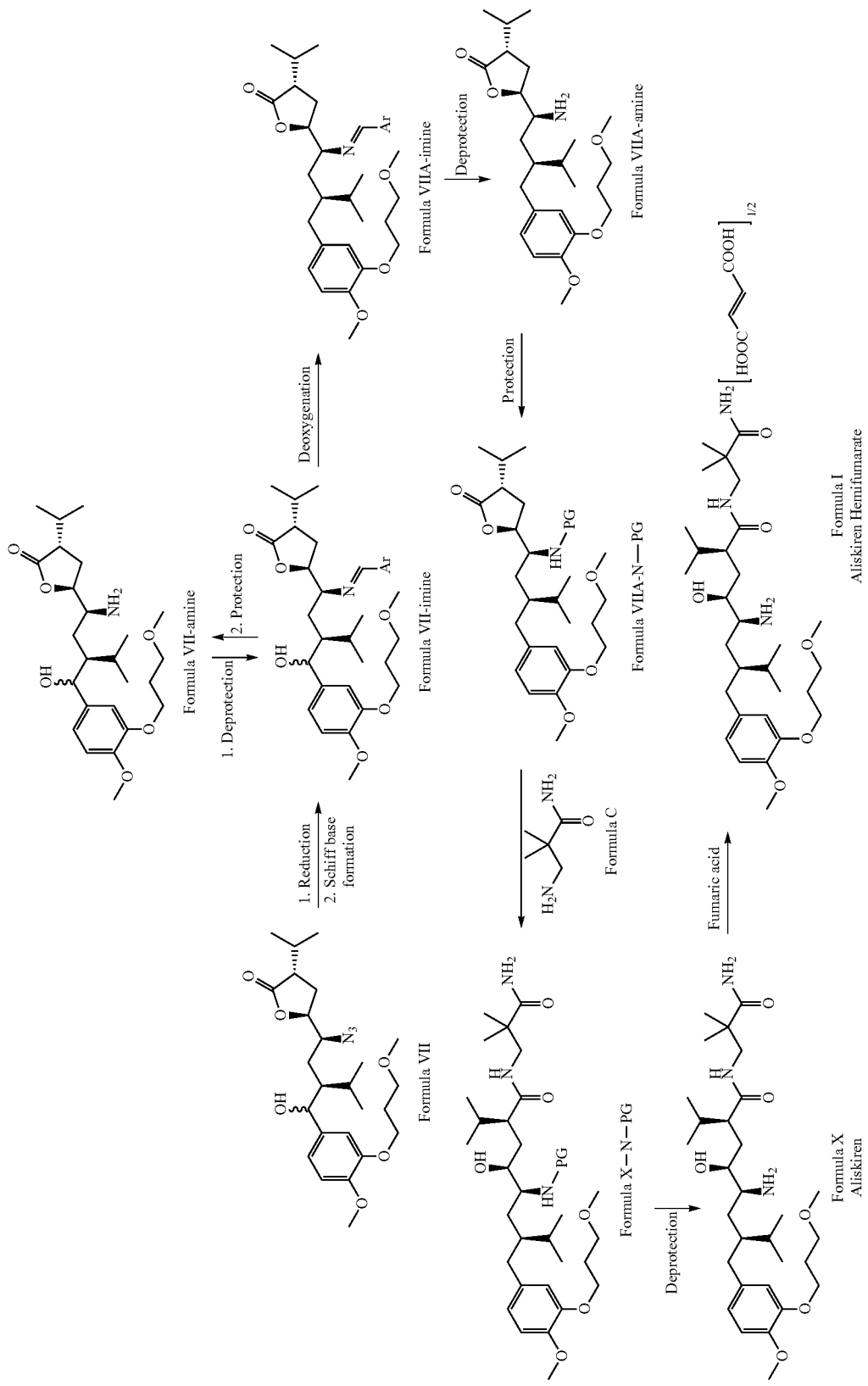
Scheme 1:
PG: Protecting group
Ar: Substituted or unsubstituted aromatic aldehyde It has been unexpectedly found that Aliskiren and its hemifumarate salt are efficiently prepared from novel intermediates (Formula VII-imine and Formula VIIA-imine) as shown in Scheme 1. These intermediates are easily isolable with better purity, which finally help in achieving Aliskiren or salt thereof, preferably hemifumarate in better yield and purity.

This process does not require any noble metal catalyst, during deoxygenation of hydroxyl group.

According to another aspect of the present invention, there is provided a novel and cost effective process for the manufacture of pure Aliskiren and its hemifumarate salt, as shown in Scheme 2.

Scheme 2:

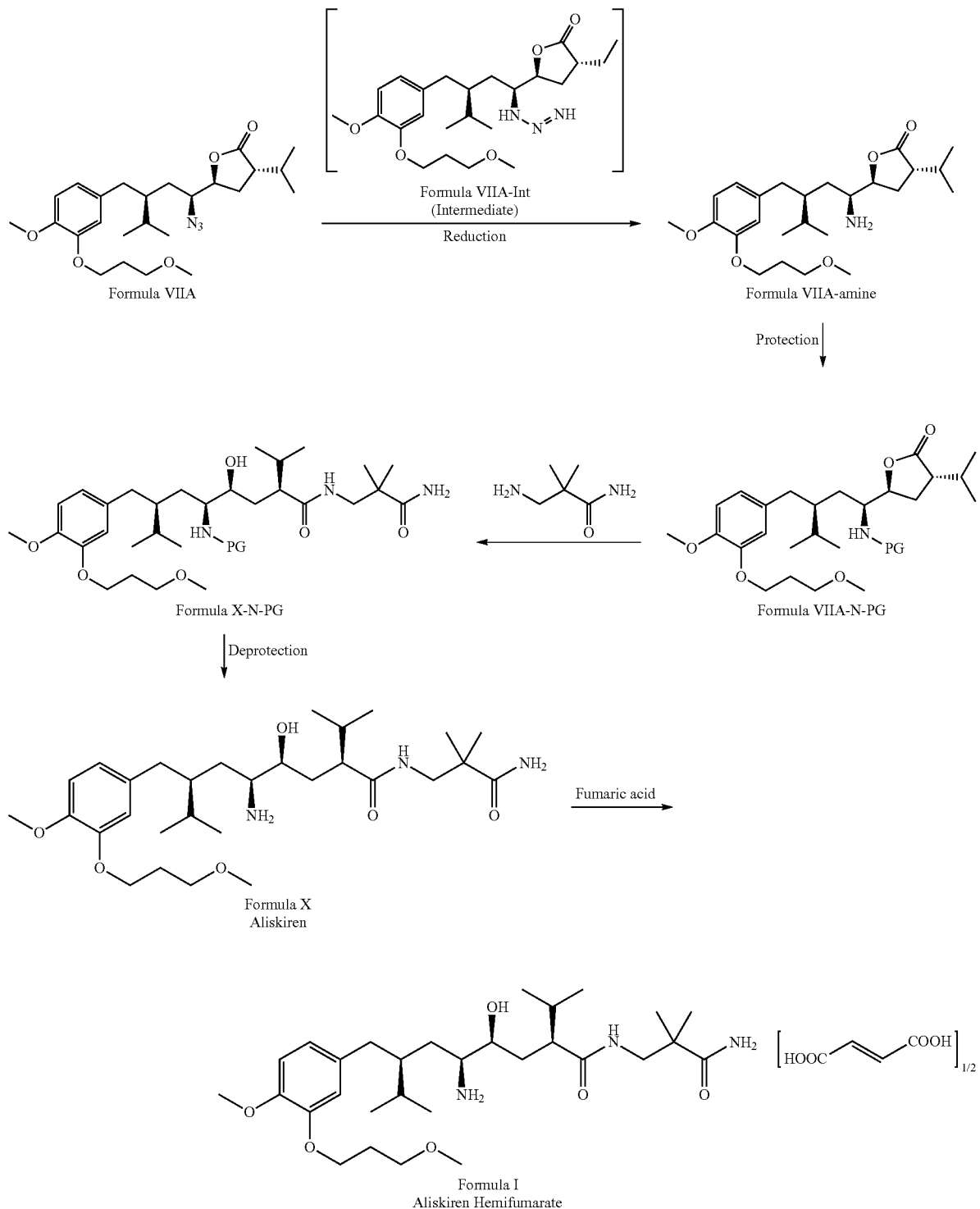

PG: Protecting group

DETAILED DESCRIPTION OF THE INVENTION

The present invention (Scheme 1) relates to a novel process for the preparation of Aliskiren or pharmaceutically acceptable salts thereof, preferably Aliskiren hemifumarate comprising the steps of:

(a) carrying out reduction by hydrogenating a compound of Formula VII

Formula VII

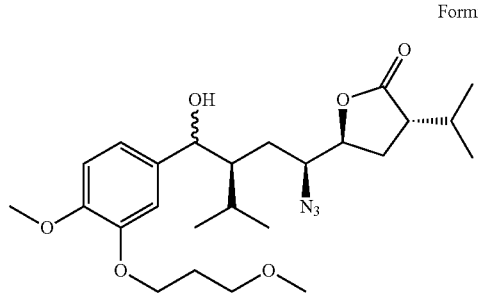

in the presence of metal catalyst followed by reaction with substituted or unsubstituted aromatic aldehyde to form Schiff base compound of Formula VII-imine. The compound of formula VII-imine can be prepared directly by reduction of the compound of formula VII in the presence of substituted or unsubstituted aromatic aldehyde with metal catalyst to obtain Schiff base compound of Formula VII-imine, which is optionally purified either by converting to compound of Formula VII-amine and reconverting to compound of Formula VII-imine or by conventional purification methods known in prior art, such as column chromatography Formula VII-imine Formula VII-amine

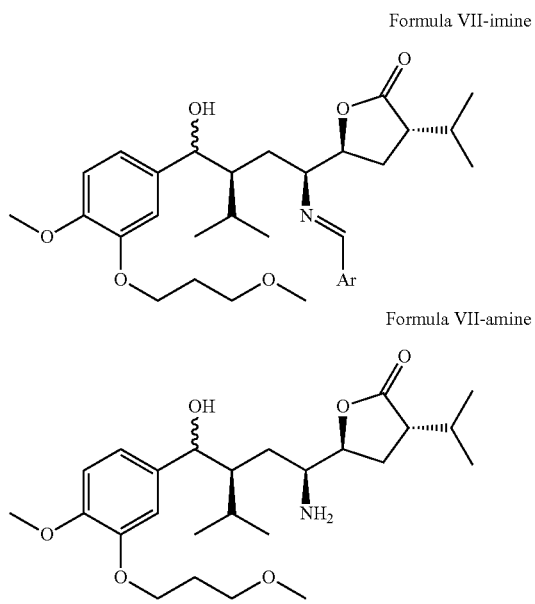

wherein Ar is substituted or unsubstituted aromatic aldehyde;
(b) carrying out deoxygenation by selectively reducing the compound of Formula VII-imine with trialkylsilane such as triethylsilane (TES) in the presence of trimethylsilyl trifluoromethanesulfonate (TMSOTf) or with triethylsilane in trifluoroacetic acid or with triethylsilane in titanium tetrachloride to obtain compound of the Formula VIIA-imine;

Formula VIIA-imine

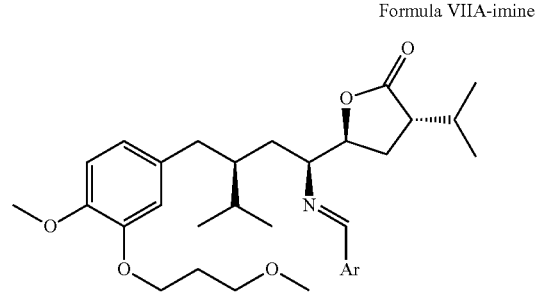

wherein Ar is substituted or unsubstituted aromatic aldehyde;
(c) deprotecting the compound of Formula VIIA-imine with inorganic acid or organic acid to obtain the compound of Formula VIIA-amine;

Formula VIIA-amine

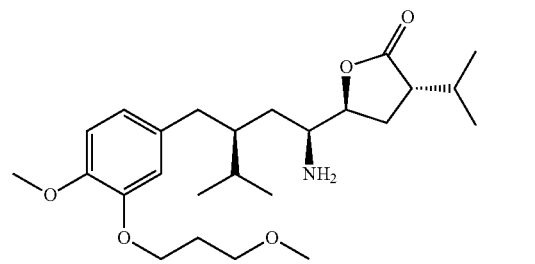

(d) protecting the compound of Formula VIIA-amine with suitable protecting group in the presence of an organic or inorganic base to obtain compound of the Formula VIIA-N-PG;

Formula VIIA-N-PG

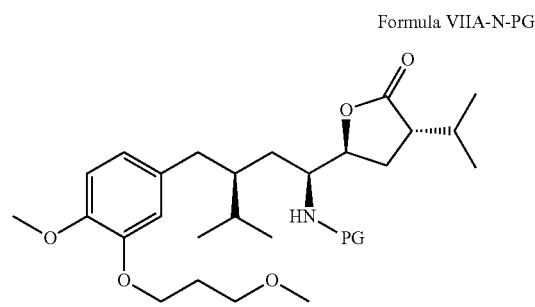

wherein PG: protecting group;
(e) reacting the compound of Formula VIIA-N-PG with compound of Formula C i.e. 3-amino-2,2-dimethylpropionamide in an organic solvent in the presence of 2-hydroxy pyridine and a base to obtain compound of the Formula X—N-PG;

Formula C

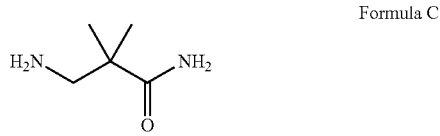

-continued

Formula X-N-PG

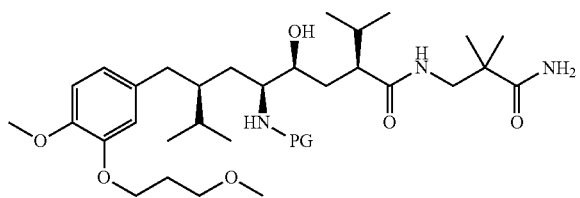

wherein PG: protecting group;
(f) deprotecting the compound of Formula X—N-PG with acid or base or catalytic hydrogenolysis using hydrogen gas or catalytic hydrogen transfer in the presence of an organic solvent to obtain Aliskiren of the Formula X and;

Formula X

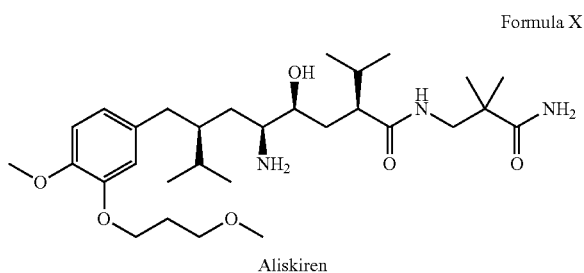

Aliskiren (g) treating Aliskiren of the Formula X with fumaric acid to obtain Aliskiren hemifumarate of Formula I.

Formula I

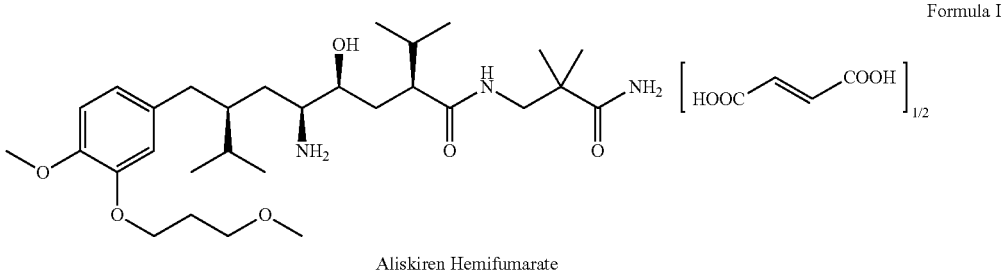

Aliskiren Hemifumarate

In step (a) of Scheme 1, hydrogenolysis of the compound of Formula VII is carried out in the presence of substituted or unsubstituted aromatic aldehyde with metal catalyst such as Pd/C, Pt/C, PtO$_2$/C, Raney/Ni in an organic solvent, wherein the organic solvent is selected from the group comprising of alcohol such as methanol, ethanol, propanol, butanol; ester such as ethyl acetate, isopropyl acetate; ether such as methyl-tert-butyl ether and the like. The substituted or unsubstituted aromatic aldehyde is selected from the group comprising of benzaldehyde, hydroxy benzaldehyde, methyl benzaldehyde, methoxy benzaldehyde, nitro benzaldehyde, fluoro benzaldehyde, chloro benzaldehyde, bromo benzaldehyde and the like. The compound of Formula VII-imine is hydrolysed with inorganic acid such as hydrofluoric acid, hydrochloric acid, hydrobromic acid, perchloric acid and phosphoric acid and the like or organic acid such as acetic acid, citric acid, oxalic acid and the like in the presence of an organic solvent such as alcohol like methanol, ethanol, propanol, butanol; ester such as ethyl acetate, isopropyl acetate; chlorinated solvent such as dichloromethane; hydrocarbon such as toluene and the like to form compound of Formula VII-amine, which is further reconverted to compound of Formula VII-imine by reacting with substituted or unsubstituted aromatic aldehyde in an organic solvents such as alcohol like methanol, ethanol, propanol, butanol; ester such as ethyl acetate, isopropyl acetate; chlorinated solvent such as dichloromethane hydrocarbon such as toluene and the like.

In step (b) of Scheme 1, the compound of Formula VII-imine is selectively reduced with trialkylsilane such as triethylsilane (TES) in the presence of trimethylsilyl trifluoromethanesulfonate (TMSOTf) in an organic solvent. The organic solvent is selected from the group comprising of chlorinated solvent such as dichloromethane, dichloroethane, chloroform, ether such as tetrahydrofuran, dioxane and hydrocarbon such as toluene and the like.

In step (c) of Scheme 1, compound of Formula VIIA-imine is deprotected using inorganic acid or organic acid in an organic solvent. The inorganic acid used is selected from hydrofluoric acid, hydrochloric acid, hydrobromic acid, perchloric acid and phosphoric acid and the like. The organic acid used is selected from acetic acid, citric acid, oxalic acid and the like. The organic solvent is selected from the group comprising of alcohol such as methanol, ethanol, propanol; ester such as ethyl acetate, isopropyl acetate; ether such as methyl tert-butyl ether, diisopropyl ether; chlorinated solvent such as dichloromethane hydrocarbon such as toluene and the like.

In step (d) of Scheme 1, amino group of the compound of Formula VIIA-amine is protected with protecting agent such as BOC anhydride, Fmoc-Cl, substituted or unsubstituted CbzCl, trityl chloride and the like in the presence of a base and an organic solvent. The base is inorganic base or organic base. The inorganic base is selected from sodium bicarbonate, sodium carbonate, potassium bicarbonate, potassium carbonate and the like. The organic base is selected from triethylamine, diisopropylethylamine, tributylamine, dicyclohexylamine, piperidine, pyridine and the like. The organic solvent is selected from the group comprising of chlorinated solvent such as dichloromethane, dichloroethane, chloroform; ester such as ethyl acetate, isopropyl acetate; ether such as methyl-tert-butyl ether, THF and the like.

In step (e) of Scheme 1, the compound of Formula VIIA-N-PG is reacted with compound of Formula C i.e. 3-amino-2,2-dimethylpropionamide in an organic solvent in the presence of 2-hydroxy pyridine and a base. The compound of Formula C is added optionally in lot-wise manner. The organic solvent is selected from the group comprising of aromatic hydrocarbon such as toluene, ether such as methyl tert-butyl ether and the like. The base is organic amine selected from the group comprising of triethylamine, diisopropylethylamine, tributylamine and the like. This reaction is optionally performed in the absence of an organic solvent.

In step (f) of Scheme 1, the compound of Formula X—N-PG is subjected to deprotection with acid or base or catalytic hydrogenolysis using hydrogen gas or catalytic hydrogen transfer in the presence of an organic solvent to obtain Aliskiren of the Formula X. The acid is selected from inorganic acid such as hydrochloric acid (aqueous or gaseous), hydrogen bromide, hydrogen fluoride, hydrogen phosphate, perchloric acid or organic acid such as trifluoroacetic acid, para-toluene sulfonic acid, methanesulfonic acid, camphor sulfonic acid and the like. The base is selected from the group comprising of metal alkoxide such as sodium ethoxide, potassium ethoxide, sodium tert-butoxide, potassium tert-butoxide and the like. The organic solvent is selected from the group comprising of ether such as dioxane, tetrahydrofuran; chlorinated solvent such as dichloromethane, dichloroethane, chloroform; ester such as ethyl acetate, isopropyl acetate; alcohol such as methanol, ethanol, propanol and the like.

In step (g) of Scheme 1, the compound of Formula X is treated with fumaric acid to yield Aliskiren hemifumarate of Formula I.

The starting material of Scheme 1 i.e. compound of Formula VII is prepared according to prior art process.

The present invention (Scheme 2) relates to a novel process for the preparation of Aliskiren or its pharmaceutically acceptable salts thereof, preferably Aliskiren hemifumarate comprising the steps of:

(i) carrying out the reduction by hydrogenating a compound of Formula VIIA with or without isolation of novel intermediate of Formula VIIA-Int, by using hydrogen gas in the presence of metal catalyst such as Pd/C, Pt/C, PtO$_2$/C, Raney/Ni, in the presence of an organic solvent to obtain the compound of Formula VIIA-amine;

Formula VIIA

Formula VIIA-Int (Intermediate)

Formula VIIA-amine (ii) protecting the compound of Formula VIIA-amine with suitable protecting agents in the presence of a base to obtain the compound of Formula VIIA-N-PG.

The compound of Formula VIIA-N-PG can be prepared directly from reduction of the compound of Formula VIIA without isolating the compound of Formula VIIA-amine and subsequently followed by addition of protecting agent.

The compound of Formula VIIA-N-PG can also be prepared directly from reduction of the compound of Formula VIIA in the presence of protecting agent without isolating the compound of Formula VIIA-amine;

Formula VIIA-N-PG wherein PG: protecting group;

(iii) reacting the compound of Formula VIIA-N-PG with compound of Formula C i.e. 3-amino-2,2-dimethylpropionamide in the presence of 2-hydroxy pyridine to obtain compound of the Formula X—N-PG

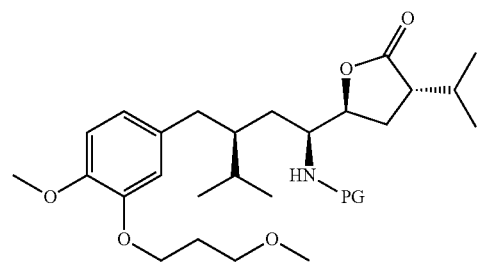

Formula C

Formula X-N-PG wherein PG: protecting group;

(iv) subjecting the said compound of Formula X—N-PG to deprotection with acid or base or catalytic hydrogenolysis using hydrogen gas or catalytic hydrogen transfer in the presence of an organic solvent to obtain Aliskiren of the Formula X and;

Formula X

Aliskiren (v) treating Aliskiren of the Formula X with fumaric acid to obtain Aliskiren hemifumarate of Formula I.

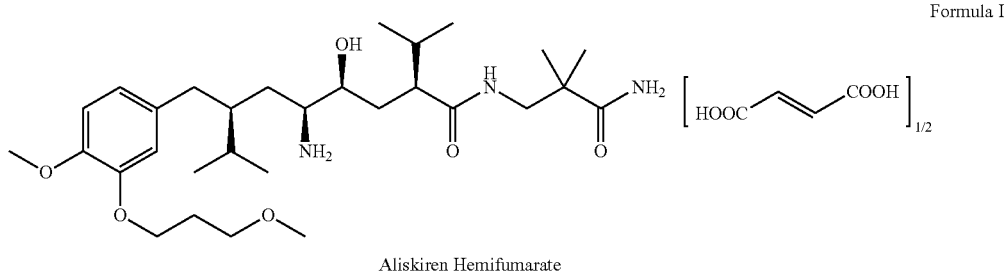

Aliskiren Hemifumarate

In step (i) of Scheme 2, hydrogenation of the compound of Formula VIIA is carried out with or without isolation of novel intermediate of Formula VIIA-Int, by using hydrogen gas in the presence of metal catalyst such as Pd/C, Pt/C, PtO$_2$/C, Raney/Ni, in the presence of an organic solvent selected from the group comprising of alcohol such as methanol; ester such as ethyl acetate, isopropyl acetate; ether such as methyl tert-butyl ether and the like. Further, the compound of Formula VIIA amine can be optionally purified by preparing its acid addition salt. Acid can be selected from the group comprising of organic acid such as oxalic acid, citric acid, fumaric acid, malic acid, succinic acid, camphorsulphonic acid, para-toluene sulphonic acid, mandelic acid, malic acid, maleic acid, The compound of Formula VIIA-N-PG can also be prepared directly from reduction of the compound of Formula VIIA in the presence of protecting agent without isolating the compound of Formula VIIA-amine. The applicant has observed that during the said preparation i.e. during reduction of the compound of Formula VIIA in the presence of protecting agent such as BOC anhydride there is a formation of a dimer impurity of Formula D, which was isolated from the reaction mixture. This impurity was also independently synthesized by coupling of compound of Formula VIIA-amine with triphosgene and confirmed by analytical techniques such as IR, $^1$H-NMR, mass spectrum, etc. The structure of the dimer impurity is as given below:

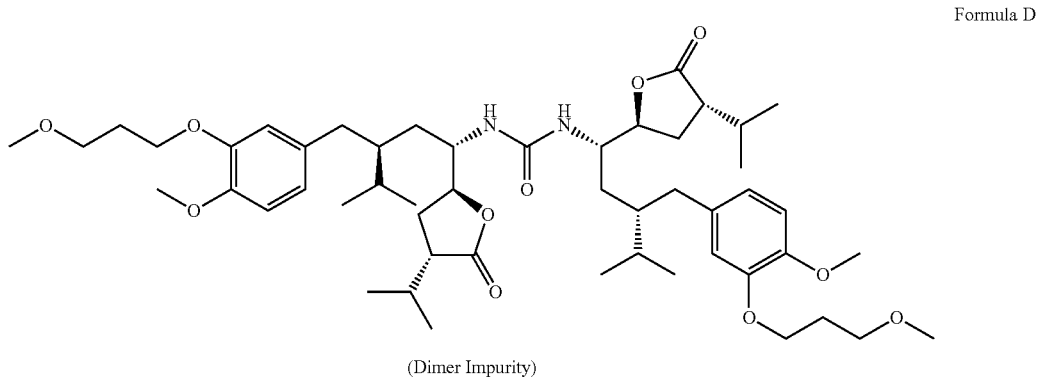

(Dimer Impurity)

tartaric acid, dibenzoyl tartaric acid, ditoluoyl tartaric acid, methane sulphoic acid or inorganic acid such as hydrochloric acid, hydrobromic acid, sulphuric acid and the like.

In step (ii) of Scheme 2, compound of Formula VIIA-amine is protected with suitable protecting agents selected from the group comprising of BOC anhydride, Fmoc-Cl, substituted or unsubstituted CbzCl, trityl chloride and the like in the presence of a base and an organic solvent to obtain the compound of Formula VIIA-N-PG. The base is selected from organic base such as triethylamine, diisopropyl ethylamine, pyridine, DMAP or inorganic base such as sodium carbonate, potassium carbonate, sodium bicarbonate and potassium bicarbonate and the like. The organic solvent is selected from the group comprising of chlorinated solvent such as dichloromethane, dichloroethane, chloroform; ester such as ethyl acetate, isopropyl acetate; ether such as methyl-tert-butyl ether, tetrahydrofuran and the like.

The compound of Formula VIIA-N-PG can be optionally purified using hydrocarbon solvent selected from the group comprising of aromatic, alicyclic or aliphatic hydrocarbon like cyclohexane, n-hexane or toluene and the like.

In step (iii) of Scheme 2, the compound of Formula VIIA-N-PG is reacted with compound of Formula C in an organic solvent in the presence of 2-hydroxy pyridine and a base. The compound of Formula C is added optionally in lot-wise manner. The organic solvent is selected from the group comprising of aromatic hydrocarbon such as toluene, ether such as methyl tert-butyl ether and the like. The base is organic amine selected from triethylamine, diisopropylethylamine, tributylamine and the like. This reaction is optionally performed in the absence of an organic solvent.

The compound of Formula X—N-PG can be optionally purified selecting either aromatic hydrocarbon or ester or aqueous alcohol or ether or mixture thereof. The aromatic hydrocarbon is selected from toluene and the like. The ester is selected form ethyl acetate, isopropyl acetate and the like. The alcohol is selected from methanol, isoproapnol, butanol and the like. The ether is selected from di-isopropyl ether, methyl-tert-butyl ether, tetrahydrofuran or dioxane and the like.

In step (iv) of Scheme 2, the compound of Formula X—N-PG is subjected to deprotection with either acid or base in the presence of an organic solvent to obtain Aliskiren of the Formula X. The acid is selected from inorganic acid such as hydrochloric acid (aqueous or gaseous), hydrogen bromide, hydrogen fluoride, hydrogen phosphate, perchloric acid or organic acid such as trifluoroacetic acid, para-toluene sulfonic acid, methanesulfonic acid, camphor sulfonic acid and the like. The base is selected from the group comprising of metal alkoxide such as sodium ethoxide, potassium ethoxide, sodium tert-butoxide, potassium tert-butoxide and the like. The organic solvent is selected from the group comprising of ether such as dioxane, tetrahydrofuran; chlorinated solvent such as dichloromethane, dichloroethane, chloroform; ester such as ethyl acetate, isopropyl acetate; alcohol such as methanol, propanol and the like.

Aliskiren of Formula X can be optionally purified by treating with aromatic hydrocarbon such as toluene in the presence of base such as aqueous solution of hydroxide, carbonate of alkali or alkaline earth metal.

In step (v) of Scheme 2, the compound of Formula X is treated with fumaric acid to yield Aliskiren hemifumarate of Formula I, which can be optionally purified using solvent selected from alcohol, nitrile, ester or mixture thereof. The alcohol is selected from the group comprising of methanol, ethanol, isopropanol and the like. The nitrile is selected from the group comprising of acetonitrile, propionitrile and the like. The ester is selected from the group comprising of ethyl acetate, isopropyl acetate and the like.

The starting material of Scheme 2 i.e. compound of Formula VIIA can be prepared according to any prior art processes.

Aliskiren and its hemifumarate salt obtained by the process of the invention is in fact substantially pure, and in particular substantially free from dimer impurity of compound of formula D. The expression "substantially pure" means having a purity degree equal to or higher than 99%.

The process for the preparation of Aliskiren and Aliskiren hemifumarate described in the present invention is demonstrated in the examples illustrated below. These examples are provided as illustration only and therefore should not be construed as limitation of the scope of the invention.

EXAMPLES

Preparation of Compound of Formula VII-Amine

To a solution of compound of Formula VII (10 g, 20.9 mmol) in methanol (100 mL) was added 5% Pd/C (2 g) and hydrogenated at 3.5 Kg pressure at room temperature for 12.0 h. After the completion of reaction, the reaction mixture was filtered through hyflo bed, washed with methanol (20 mL) and the filtrate was distilled under vacuum at 45-50° C. The oil thus formed, was dissolved in ethyl acetate (25 mL) and extracted first with dilute hydrochloric acid (2.19 g in 25 mL water) and again with dilute hydrochloric acid (0.55 g in 6.25 mL water) at room temperature. The combined aqueous layer was washed with ethyl acetate (12.5 mL) and the pH of aqueous layer was adjusted to 11.5-12.0 using 2.0 N sodium hydroxide solution (6.0 mL). Aqueous layer was then extracted with ethyl acetate (2×25 mL) and the combined organic layer was washed with water (25.0 mL) and distilled under vacuum at 45-50° C. and degassed for 15.0 min to afford 3.0 g of title compound. (Yield: 32%)

Preparation of Compound of Formula VII-Imine (Benzaldehyde Imine Compound)

To a stirred solution of compound of Formula VII-amine (1.4 g, 3.1 mmol) and methanol (14 mL), added benzaldehyde (0.32 g, 3.1 mmol) at room temperature and the reaction mass was stirred for 1 hr. Solvent was recovered at 40-45° C. under vacuum completely to furnish 1.6 g of the desired imine derivative. (Yield: 96%)

Preparation of Compound of Formula VII-Imine (Salicylaldehyde Imine Compound)

Compound of Formula VII-amine (0.2 g, 0.44 mmol) was stirred with methanol (1 mL) and a solution of salicyladehyde (0.06 g, 0.49 mmol) in methanol (1 mL) was added to it at room temperature. The reaction mass was stirred at room temperature for another 2 hr and the solvent was recovered at 40-45° C. under vacuum completely. The crude mass thus obtained was dissolved in dichloromethane (2 mL) and washed successively with DM water (2 mL) and saturated solution of sodium bicarbonate (2×2 mL). The organic layer was evaporated to dryness and the residue was purified by column chromatography using silica gel and 20% ethyl acetate/hexanes mixture to furnish 0.18 g of the desired imine. (Yield: 73%)

Preparation of Compound of Formula VII-Imine

To a solution of compound of Formula VII (10 g, 0.021 mol) in methanol (100 mL) was added 10% Pd/C (50% wet, 1.0 g) and benzaldehyde (2.22 g, 0.021 mol) and hydrogenated at 3 Kg pressure at room temperature. After the completion of the reaction, the reaction mixture was filtered through hyflo bed, washed with methanol (2×10 mL) and the filtrate was distilled under vacuum at 45-50° C. The resulting oil was taken in ethyl acetate (50 mL) and extracted with 10% aq. citric acid solution (2×50 mL) for 15 min at room temperature. The combined aqueous layer was basified to a pH around 10.0-11.0 using 20% sodium hydroxide solution and extracted with ethyl acetate (2×50 mL). Distillation of ethyl acetate layer under vacuum at 45-50° C. afforded compound of Formula VII-amine as oil (6.2 g). Methanol (62 mL) and benzaldehyde (1.6 g, 0.15 mol) were added to above oil and stirred for 1.0 h at room temperature. After the completion of the reaction, methanol was distilled under vacuum at 45-50° C. and degassed for 30 min to afford compound of Formula VII-imine as pale yellow oil (7.4 g, 65%)

Preparation of Compound of Formula VIIA-Imine

Triethylsilane (7.76 g, 0.066 mol) was added to a solution of above oil (compound of Formula VII-imine) (7.2 g, 0.013 mol) in dichloromethane (144 mL) at room temperature. The solution was cooled to −75 to −78° C. and TMSOTf (4.45 g, 0.02 mol) was added dropwise in 15-20 min at the same temperature. After the completion of the reaction (TLC, 1.0 h), the reaction mixture was warmed to 0-5° C. and quenched with saturated aq. ammonium chloride solution (72 mL). The layers were separated and dichloromethane was distilled under reduced pressure to afford compound of Formula VIIA-imine as pale yellow oil (6.7 g, 96%).

Preparation of Compound of Formula VIIA-N—BOC

A solution of compound of Formula VIIA-imine (6.5 g, 0.012 mol) in 65 mL of methanol was treated with 2N hydrochloric acid (26 mL) at room temperature. The reaction mass was warmed to 50-55° C. and stirred for 2.0 h. After the completion of the reaction (TLC, 2.0 h), methanol was distilled off completely under vacuum and the resulting oil was taken in water (26 mL) and diisopropyl ether (26 mL). The diisopropyl ether washings were discarded and the aqueous layer was basified around pH 10.5-11.0 using 20% sodium hydroxide solution. The aqueous layer was extracted with dichloromethane (2×26 mL), dried over anhydrous sodium sulphate then filtered. To the filtrate triethylamine (1.38 g, 0.014 mol) and BOC anhydride (2.85 g, 0.013 mol) were added at room temperature and the reaction mass was stirred for 3.0 h. Water (6.5 mL) was added followed by addition of 1N hydrochloric acid (13 mL), stirred for 5 min and the layers were separated. The dichloromethane layer was washed with saturated aq. sodium bicarbonate solution (13 mL) and evaporated under reduced pressure at 40-45° C. to afford the title compound as colorless oil (5.9 g, 89%).

Preparation of Compound of Formula VIIA-Amine

To a mixture of compound of Formula VIIA (3.0 g, 0.0065 mol) and ammonium formate (0.81 g, 0.013 mol) in methanol (30 mL) was added. 10% Pd/C (50% wet, 0.3 g) at room temperature and stirred at 60-65° C. for 3 h. After cooling to room temperature, the reaction mass was filtered through hyflo and concentrated. The resulting crude mass was dissolved in dichloromethane (30 ml) and was washed with water (2×6 mL). Dichloromethane layer was evaporated to dryness to yield 2.5 g (89%) of compound of Formula VIIA amine as oil.

Preparation of Compound of Formula VIIA-Int

In a clean and dry 250 mL SS Parr shaker bottle, compound of Formula VIIA (5.0 g) was dissolved in methyl tert-butyl ether (50 mL) and 10% Pd/C (0.5 g, 50% wet) was added at room temperature. It was hydrogenated under 3.0 kg/cm$^2$ pressure at RT for 3.0-4.0 h till the complete consumption of compound of Formula VIIA. The reaction mass was filtered through hyflobed and washed with methyl tert-butyl ether (10 mL). The filtrate was evaporated under reduced pressure to yield oil which was purified by combi-flash chromatography to afford pure compound of Formula VIIA-Int as a colorless to pale yellow oil.

FT-IR (KBr): 3434, 2957, 2931, 2873, 1765, 1513, 1462, 1259, 1235, 1161, 1137, 1120, 1025, 772 cm$^{-1}$.

ESI-MS (m/z): 464 [M+H]$^+$, 486 [M+Na]$^+$, 436 [M−27]$^+$, 419 [M−N$_3$H$_2$]$^+$.

$^1$H-NMR (CDCl$_3$, δ): 6.76-6.79 (m, 1H), 6.64-6.74 (m, 2H), 4.08-4.54 (m, 3H), 3.83 (s, 3H), 3.56-3.63 (m, 2H), 3.37 (s, 3H), 2.47-2.57 (m, 2H), 2.36-2.43 (m, 1H), 2.09-2.17 (m, 3H), 1.95-2.05 (m, 1H), 1.84-1.93 (m, 2H), 1.70-1.75 (m, 1H), 1.59-1.67 (m, 1H), 1.38-1.42 (m, 1H), 1.24-1.33 (m, 2H), 1.00 (t, J=6.8 Hz, 3H), 0.93 (t, J=6.4 Hz, 3H), 0.88 (dd, J=4.0 & 6.8 Hz, 3H), 0.83 (d, J=6.8 Hz, 2H), 0.80 (d, J=6.8 Hz, 2H).

Preparation of Compound of Formula VIIA-Amine

In a clean and dry 250 ml SS Parr shaker bottle, compound of formula VIIA (5.0 g) was dissolved in methyl tert-butyl-ether (25 mL) and 10% Pd/C (0.5 g, 50% wet) was added at room temperature. It was hydrogenated under 3.0 kg/cm$^2$ pressure at room temperature for 6-8 h till the complete consumption of compound of Formula VII-A-Int. The reaction mass was filtered through hyflobed and washed with methyl tert-butyl-ether (15 mL). The filtrate was evaporated under reduced pressure at 40-45° C. to afford title compound as colorless oil (4.5 g, 95.7%).

Preparation of Compound of Formula VIIA-Amine-Oxalate Salt

Compound of Formula VIIA-amine (1.0 g, 0.0022) and oxalic acid dihydrate (0.29 g, 0.0022) were dissolved in ethyl acetate (15 ml) at 40-50° C. The reaction mixture was allowed to cool slowly to room temperature and stirred for further 3-4 h. The reaction mass was filtered under nitrogen and solid was suck dried for 10 min. under nitrogen and dried for 12 h under vacuum at 40-50° C. to afford white solid (1.1 g, 85.2%).

Preparation of Compound of Formula VIIA-N—BOC

Triethylamine (0.26 g, 0.025 mol) and BOC anhydride (0.53 g, 0.024 mol) were added to a solution of compound of Formula VIIA-amine (1.0 g, 0.0023 mol) in dichloromethane (10 mL) at room temperature. The reaction mass was stirred for a period of 3.0 h at room temperature till the consumption of starting material (TLC) water (5.0 mL) was added followed by 1N hydrochloric acid (5.0 mL), stirred for 5 min and the layers were separated. The dichloromethane layer was washed with saturated sodium bicarbonate solution (5.0 mL), separated and evaporated under reduced pressure at 40-45° C. to afford the title compound as colorless oil (1.2 g, 97%).

Preparation of Compound of Formula VIIA-N—BOC

Potassium carbonate (2.53 g, 0.183 mol) solution in DM water (24 mL) was added to a solution of Formula VIIA-amine (4.0 g, 0.0092 mol) in methyl tert-butyl-ether (32 mL) at room temperature. Resulted biphasic reaction mass was cooled to 10-15° C. and to this BOC anhydride (2.2 g, 0.0101 mol) solution in methyl-tert-butyl ether (4 mL) was added at 10-15° C. The reaction mass was warmed to room temperature and stirred for 2-3 h at 25-30° C. till the complete consumption of starting material (TLC). The methyl tert-butyl-ether layer was separated and evaporated under reduced pressure at 40-45° C. to afford title compound as colorless oil, which was crystallized from cyclohexane at 10-15° C. to give title compound as colorless solid (4.1 g, 83.5%).

Preparation of Compound of Formula VIIA-N—BOC

A solution of compound of Formula VIIA (1.0 g. 0.0021 mol), triethylamine (0.285 g, 0.0028 mol) and BOC anhydride (0.568 g, 0.0026 mol) in ethyl acetate (10 mL) was taken in a Parr apparatus. 10% Pd/C (50% wet, 0.1 g) was added under nitrogen. The mixture was stirred at room temperature for 6 h under 3 Kg hydrogen pressure. Reaction mass was filtered through hyflo bed, washed with ethyl acetate (2×5 mL). The filtrate was concentrated to dryness under vacuum at 50° C. to furnish crude solid, which was re-crystallized from cyclohexane (2 mL) at room temperature to provide the title compound as a white solid (0.8 g, 69%).

Preparation of Compound of Formula VIIA-Amine & Formula VIIA-N—BOC

In a clean and dry 250 ml SS Parr shaker bottle, compound of formula VIIA (5.0 g) was dissolved in methyl tert-butyl-ether (25 mL) and 10% Pd/C (0.5 g, 50% wet) was added at room temperature. It was hydrogenated under 3.0 kg/cm$^2$ pressure at room temperature for 6-8 h till the complete consumption of compound of Formula VII-A-Int. The reaction mass was filtered through hyflobed and washed with methyl tert-butyl-ether (15 mL). Potassium carbonate (3.0 g, 0.0216 mol) solution in DM water (30 mL) were added to a solution of Formula VIIA-amine obtained as filtrate in methyl-tert-butyl ether at room temperature. Resulted biphasic reaction mass was cooled to 10-15° C. and to this BOC anhydride (2.6 g, 0.0119 mol) solution in methyl-tert-butyl ether (5 mL) was added at 10-15° C. The reaction mass was warmed to room temperature and stirred for 2-3 h at 25-30° C. till the complete consumption of starting material (TLC). The methyl tert-butyl-ether layer separated and evaporated under reduced pressure at 40-45° C. to afford title compound as colorless oil, which was crystallized from cyclohexane at 10-15° C. to give title compound as colorless solid (5.1 g, 86.2%).

Preparation of Compound of Formula D (Dimer Impurity)

To a stirred cold solution of compound of Formula VIIA-amine (1.2 g, 0.0027 mol) and triethylamine (0.4 mL, 0.0028 mol) in dichloromethane (12 mL) was added a solution of triphosgene (0.114 g, 0.00038 mol) in dichloromethane (6 mL) dropwise over a period of 10-15 min at 0-5° C. The reaction mass was gradually warmed to room temperature and stirred overnight. After completion of the reaction (TLC, 16 h), water was added at room temperature and the layers were separated. The dichloromethane layer was completely evaporated under vacuum and the oil was redissolved in toluene (12 mL). The toluene layer was washed with 2N hydrochloric acid (2×12 mL) and distilled under reduced pressure to provide a yellow viscous oil which was purified by column chromatography on silica gel to afford the desired product as colorless oil (0.75 g, 61%).

FT-IR (KBr): 3399, 3338, 2958, 2931, 2874, 1769, 1751, 1677, 1544, 1514, 1466, 1442, 1259, 1238, 1161, 1138, 1121, 1029 cm-1.

ESI-MS (m/z): 897 $[M+H]^+$, 914 $[M+NH4]^+$ 919 $[M+Na]^+$.

$^1$H-NMR (CDCl3, δ): 6.85 (s, 2H), 6.70-6.75 (m, 4H), 5.48 (d, J=9.6 Hz, 2H), 4.43 (dd, J=5.2 &8.4 Hz, 2H), 4.07-4.20 (m, 6H), 3.81 (s, 6H), 3.54-3.59 (m, 4H), 3.31 (s, 6H), 2.72 (dd, J=3.2 & 13.2 Hz, 2H), 2.29-2.38 (m, 4H), 2.05-2.15 (m, 6H), 1.94-2.03 (m, 4H), 1.64-1.72 (m, 2H), 1.37-1.41 (m, 2H), 1.13-1.25 (m, 4H), 0.84 (d, J=9.2 Hz, 6H), 0.76 (d, J=6.8 Hz, 12H), 0.70 (d, J=6.8 Hz, 6H).

Preparation of Compound of Formula X—N—BOC

A mixture of compound of Formula VIIA-N—BOC (5.8 g, 0.011 mol), 3-amino-2,2-dimethylpropionamide (6.28 g, 0.054 mol), 2-hydroxypyridine (1.03 g, 0.011 mol) and triethylamine (17.4 mL) were heated to 65° C. After 36 h stirring at 60-65° C., the reaction mass was cooled to room temperature, diluted with water (11.6 mL), and acidified to pH 3.0-4.0 by dropwise addition of 1N hydrochloric acid (29 mL). The aqueous layer was extracted with dichloromethane (2×20 mL), washed with saturated aqueous sodium bicarbonate solution (11.6 mL), separated and evaporated under reduced pressure at 40-45° C. to afford the title compound as a foamy mass (6.0 g, 85%), which was crystallized from toluene to give a white solid.

Preparation of compound of Formula X—N—BOC

A mixture of compound of Formula VIIA-N—BOC (5.0 g, 0.0093 mol), 3-amino-2,2-dimethylaminopyridine (2.16 g 0.0187 mol), 2-hydroxypyridine (0.88 g, 0.0093 mol), triethylamine (5 mL) and methyl-tert-butyl ether (5 mL) were heated to 65-70° C. for 48 h. Resulted reaction mass was cooled to 40-45° C. and added 3-amino-2,2-dimethylaminopyridine (1.08 g, 0.0093 mol) and reaction mass was heated to 65-70° C. for 12 h. The reaction mass was cooled to room temperature, added ethylacetate (50 mL) and acidified with 20% aqueous potassium hydrogen sulphate solution (~50 mL). The aqueous layer was extracted with ethylacetate (25 mL), combined ethylacetate layer was washed with 1N sodium hydroxide solution (25 mL), separated and evaporated under reduced pressure at 40-45° C. to afford title compound as solid, which was crystallized from 50% aqueous methanol (100 mL) followed by methyl-tert-butyl ether crystallization to give white solid (5.0, 83.3%).

Preparation of Compound of Formula X—N—BOC

A mixture of compound of Formula VIIA-N—BOC (5.0 g, 0.0093 mol), 3-amino-2,2-dimethylaminopyridine (2.16 g, 0.0279 mol), 2-hydroxypyridine (0.88 g, 0.0093 mol), triethylamine (5 mL) and methyl-tert-butyl ether (5 mL) were heated to 65-70° C. for 60 h. The reaction mass was cooled to room temperature, added ethylacetate (50 mL) and acidified with 20% aqueous potassium hydrogen sulphate solution (~50 mL). The aqueous layer was extracted with ethylacetate (25 mL), combined ethylacetate layer was washed with 1N sodium hydroxide solution (25 mL), separated and evaporated under reduced pressure at 40-45° C. to afford title compound as solid, which was crystallized from 50% aqueous methanol (100 mL) followed by methyl-tert-butyl ether crystallization to give white solid (4.6, 75%).

Preparation of Compound of Formula X—N—BOC

A solution of compound of Formula VIIA (1.0 g. 0.0021 mol), triethylamine (0.285 g, 0.0028 mol) and BOC anhydride (0.568 g, 0.0026 mol) in ethyl acetate (10 mL) was taken in a Parr apparatus. 10% Pd/C (50% wet, 0.1 g) was added under nitrogen. The mixture was stirred under hydrogen pressure (3 Kg/cm$^2$) at room temperature for 6 h. After completion of reaction catalyst was filtered over hyflo bed, washed with ethyl acetate (2×5 mL). The combined filtrate was concentrated under vacuum at 50° C. to furnish compound of Formula VIIA-N—BOC, which was used in the next step as such. To the oily mass compound of Formula C (0.754 g, 0.0065 mol), 2-hydroxy pyridine (0.2 g (0.0021 mol) and triethylamine (3 mL) was added and stirred at 60-65° C. for 36 h. After cooling to room temperature, water (5 mL) was added and adjusted its pH to 5 with acetic acid (1.0 mL) and again adjusted its pH to 2-3 with solid citric acid (1.5 g) followed by addition of ethyl acetate (10 mL). The mixture was stirred for 5 min and the layers were separated. The aqueous layer was extracted with ethyl acetate (5 mL). The combined ethyl acetate layer was washed with water (5 mL) and concentrated to dryness under vacuum to furnish oil (1.26 g). This was taken in toluene (10 mL) and stirred at 85-90° C. for 30 min, gradually cooled to room temperature and then to 0° C. After stirring at 0 to 5° C. for 2 h, the solid was filtered, washed with chilled toluene (5 mL) and dried under vacuum at 50° C. to afford 0.92 g (53%) of the product.

Preparation of Compound of Formula X (Aliskiren)

A solution of compound of Formula X—N—BOC (2.0 g, 0.0031 mol) in 1,4-dioxane (8.0 mL) was cooled to 0-5° C. 4M dioxane/hydrochloric acid (2.3 mL) was added dropwise over a period of 5-10 min at 0-5° C. The reaction was stirred for 15 min at 0-5° C. and warmed to room temperature. After completion of the reaction (TLC, 4.0 h), solvents were evaporated under vacuum and the crude mass was taken in water (8 mL) at 45-50° C. The aqueous layer was washed with ethyl acetate (2×10 mL), and basified to pH 11.0-12.0 using 20% sodium hydroxide solution. After ethyl acetate extraction (2×15 mL), the solvents were distilled off under vacuum at 45-50° C. to afford Aliskiren free base as colorless oil (1.5 g, 89%), Impurity D: Not detected.

Preparation of Compound of Formula X

A solution of compound of Formula X—N—BOC (5.0 g, 0.0077 mol) in dichloromethane (50 mL) was cooled to 0-5° C. Conc. HCl (6.6 mL, 0.0770 mol) was slowly added at 0-5° C. and stirred reaction mass at 0-5° C. for 3 h. After completion of reaction (TLC), 20% aqueous sodium carbonate (42 mL) was added at 0-5° C. and warmed to room temperature. The aqueous layer was extracted with dichloromethane (50 mL) and combined dichloromethane was washed with DM water (50 mL). The solvent was distilled off under reduced pressure at 40-45° C. to afford Aliskiren free base as colorless oil. Added toluene (50 mL) and heated to 40-45° C. Washed toluene layer with 1% sodium hydroxide solution (25 mL) at 40-45° C., separated and evaporated under reduced pressure at 40-45° C. to afford Aliskiren free base as colorless oil (3.8, 90.4%).

Preparation of Compound of Formula I (Aliskiren Hemifumarate)

Aliskiren i.e. compound of Formula X (1.5 g, 0.003 mol) and fumaric acid (0.15 g, 0.0013 mol) were dissolved in 5% ethanol/acetonitrile (7.5 mL) and heated to 50-55° C. for 15 min. The reaction mixture was allowed to cool slowly to room temperature and stirred for further 12 h. The slurry formed was diluted with 5% ethanol/acetonitrile (7.5 mL) and filtered under nitrogen. The solid was suck dried for 10 minute under nitrogen and dried for 12 h under vacuum at room temperature to afford white solid (0.9 g, 54%).

Preparation of Compound of Formula I (Aliskiren Hemifumarate)

Compound of Formula X (4.0, 0.0073 mol) and fumaric acid (0.40 g, 0.0025) were dissolved in methanol (20 ml) added charcoal and passed through hyflo and filtrate was concentrated at 40-45° C. under reduced pressure to afford title compound as foaming solid. The foaming solid were dissolved in 5% ethanol/acetonitrile (100 mL) and heated to 50-55° C. for 15 minute. The reaction mixture was allowed to cool slowly to room temperature and stirred for further 12 h. The reaction mass was filtered under nitrogen and solid was suck dried for 10 minute under nitrogen and dried for 12 h under vacuum at 40-50° C. to afford white solid (3.6 g, 81.5%), Impurity D: Not detected.

Preparation of Compound of Formula I

A solution of compound of Formula X—N—BOC (5.0 g, 0.0077 mol) in dichloromethane (50 mL) was cooled to 0-5° C. Concentrated hydrochloric acid (6.6 mL, 0.0770 mol) was slowly added at 0-5° C. and stirred reaction mass at 0-5° C. for 3 h. After completion of reaction (TLC), 20% aqueous sodium carbonate (42 mL) was added at 0-5° C. and warmed to room temperature. The aqueous layer was extracted with dichloromethane (50 mL) and combined dichloromethane was washed with DM water (50 mL). The solvent were distilled off under reduced pressure at 40-45° C. to afford Aliskiren free base as colorless as oil. To oily residue methanol (25 mL) and fumaric acid (0.42 g, 0.0036) were added and dissolved at 40-45° C. Solvent were removed at 40-45° C. under reduced pressure to afford title compound as foaming solid. The foaming solid were dissolved in 5% ethanol/acetonitrile (125 mL) and heated to 50-55° C. for 15 minute. The reaction mixture was allowed to cool slowly to room temperature and stirred for further 12 h. The reaction mass was filtered under nitrogen and solid was suck dried for 10 minute. under nitrogen and dried for 12 h under vacuum at 40-50° C. to afford white solid (3.8 g, 85.6%).

The invention claimed is:

1. A process for the preparation of Aliskiren hemifumarate of Formula I, comprising the steps of:

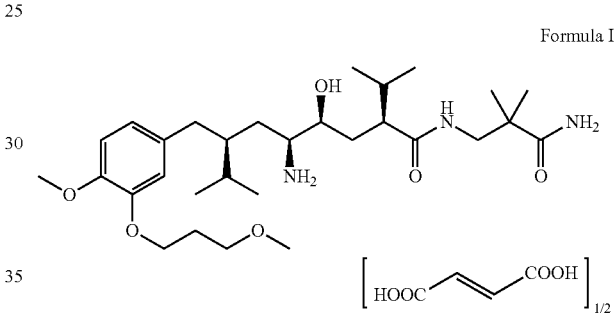

Formula I (i) reducing the compound of Formula VIIA with or without isolation of intermediate of Formula VIIA-Int, to obtain the compound of Formula VIIA-amine, which can be optionally converted to acid-addition salt thereof;

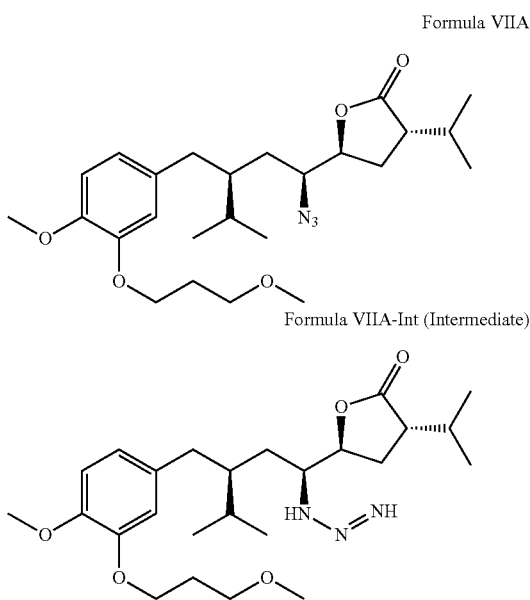

Formula VIIA

Formula VIIA-Int (Intermediate)

Formula VIIA-amine

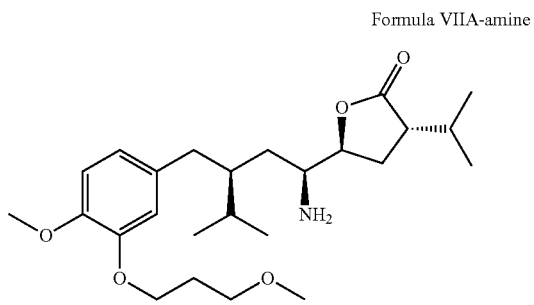

(ii) protecting the compound of Formula VIIA-amine with a suitable protecting agent in the presence of a base to obtain the compound of Formula VIIA-N-PG, Formula VIIA-N-PG

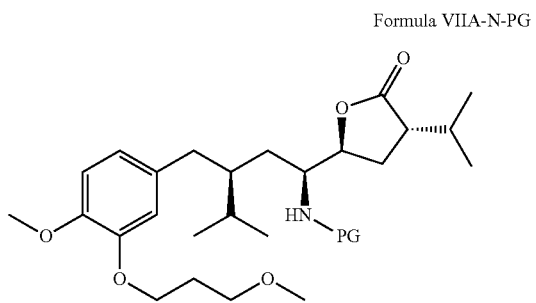

wherein PG is a protecting group selected from the group consisting of BOC, FMOC, substituted or unsubstituted Cbz and trityl;

(iii) reacting the compound of Formula VIIA-N-PG with compound of Formula C in presence of 2-hydroxy pyridine and base to obtain compound of the Formula X—N-PG Formula C Formula X-N-PG

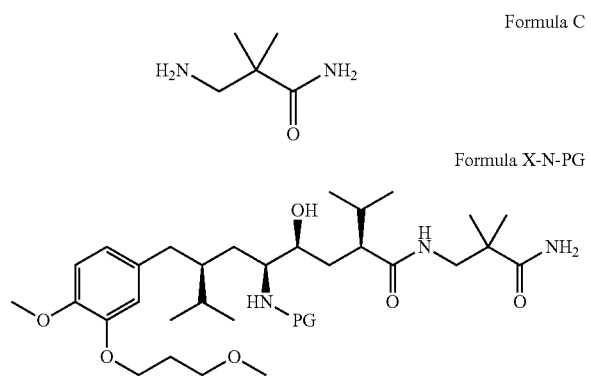

wherein PG is a protecting group selected from the group consisting of BOC, FMOC, substituted or unsubstituted Cbz and trityl;

(iv) deprotecting the compound of Formula X—N-PG with acid or base or catalytic hydrogenolysis using hydrogen gas or catalytic hydrogen transfer in presence of organic solvent to obtain Aliskiren of the Formula X Formula X

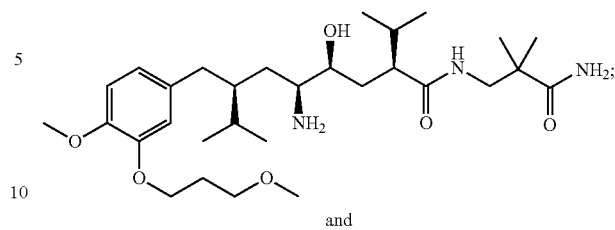

and (v) treating Aliskiren of the Formula X with fumaric acid to obtain Aliskiren hemifumarate of Formula I.

2. The process according to claim 1, wherein reduction in step (i) is carried out using a metal catalyst selected from group consisting of Pd/C, Pt/C, $PtO_2$/C and Raney/Ni.

3. The process according to claim 1, wherein reduction in step (i) is carried out in the presence of an organic solvent selected from the group consisting of an alcohol selected from the group consisting of methanol, ethanol, propanol and butanol; an ester selected from the group consisting of ethyl acetate, isopropyl acetate; and methyl-tert-butyl ether.

4. The process according to claim 1, wherein acid-addition salt in step (i) is prepared by using an acid selected from the group consisting of an organic acid selected from the group consisting of oxalic acid, citric acid, fumaric acid, malic acid, succinic acid, camphorsulphonic acid, para-toluene sulphonic acid, mandelic acid, malic acid, maleic acid, tartaric acid, dibenzoyl tartaric acid, ditoluoyl tartaric acid and methane sulphoic acid; and an inorganic acid selected from the group consisting of hydrochloric acid and hydrobromic acid.

5. The process according to claim 1, wherein the protecting agent in step (ii) is selected from the group consisting of BOC anhydride, FMOC-Cl, substituted or unsubstituted CbzCl and trityl chloride.

6. The process according to claim 1, wherein the base in step (ii) is selected from the group consisting of an organic base selected from the group consisting of triethylamine, diisopropylethylamine, pyridine and DMAP; and an inorganic base selected from the group consisting of sodium carbonate, potassium carbonate, sodium bicarbonate and potassium bicarbonate.

7. The process according to claim 1, wherein protection in step (ii) is carried out in the presence of an organic solvent selected from the group consisting of chlorinated solvent selected from the group consisting of dichloromethane, dichloroethane and chloroform an ester selected from the group consisting of ethyl acetate and isopropyl acetate; and an ether selected from the group consisting of methyl-tert-butyl ether and tetrahydrofuran.

8. The process according to claim 1, wherein the compound of Formula VIIA-N-PG is prepared directly from reduction of the compound of Formula VIIA without isolating the compound of Formula VIIA-amine followed by addition of protecting agent.

9. The process according to claim 1, wherein the compound of Formula VIIA-N-PG is prepared directly from reduction of the compound of Formula VIIA in presence of protecting agent.

10. The process according to claim 1, wherein the reaction in step (iii) is carried out in the presence of the organic solvent selected from the group consisting of aromatic hydrocarbon selected from the group consisting of toluene and methyl tert-butyl ether.

11. The process according to claim 1, wherein the base in step (iii) is selected from the group consisting of triethylamine, diisopropylethylamine and tributylamine.

12. The process according to claim 1, wherein the acid used in step (iv) is selected from the group consisting of an inorganic acid selected from the group consisting of hydrochloric acid, hydrogen bromide, hydrogen fluoride, hydrogen phosphate and perchloric acid; and an organic acid selected from the group consisting of trifluoroacetic acid, para-toluene sulfonic acid, methanesulfonic acid and camphor sulfonic acid.

13. The process according to claim 1, wherein base used in step (iv) is selected from the group consisting of a metal alkoxide selected from the group consisting of sodium ethoxide, potassium ethoxide, sodium tert-butoxide and potassium tert-butoxide.

14. The process according to claim 1, wherein the organic solvent used in step (iv) is selected from the group consisting of an ether selected from the group consisting of dioxane and tetrahydrofuran; a chlorinated solvent selected from the group consisting of dichloromethane, dichloroethane and chloroform; an ester selected from the group consisting of ethyl acetate and isopropyl acetate; and an alcohol selected from the group consisting of methanol, ethanol and propanol.

15. The process according to claim 1, wherein the reaction of step (v) is carried out in presence of an organic solvent selected from the group consisting of an alcohol selected from the group consisting of methanol, ethanol and isopropanol; a nitrile selected from the group consisting of acetonitrile and propionitrile; an ester selected from the group consisting of ethyl acetate and isopropyl acetate; and a mixture thereof.

16. A process for the preparation of Aliskiren hemifumarate of Formula I, comprising the steps of:

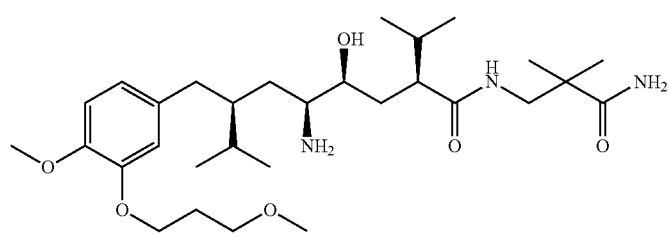

Formula I (a) reducing the compound of Formula VII in organic solvent

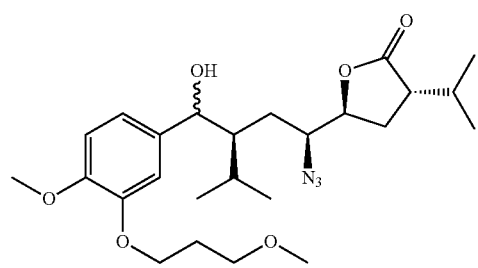

Formula VII followed by reaction with substituted or unsubstituted aromatic aldehyde to form Schiff base compound of Formula VII-imine or reducing the compound of formula VII in presence of substituted or unsubstituted aromatic aldehyde to obtain Schiff base compound of Formula VII-imine, which is optionally purified either by converting to compound of Formula VII-amine and reconverting to compound of Formula VII-imine;

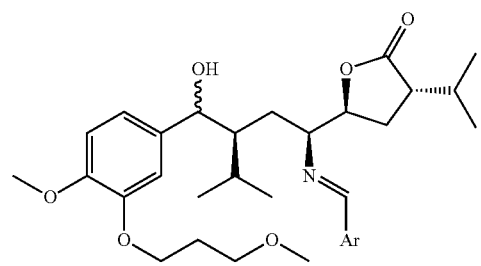

Formula VII-imine

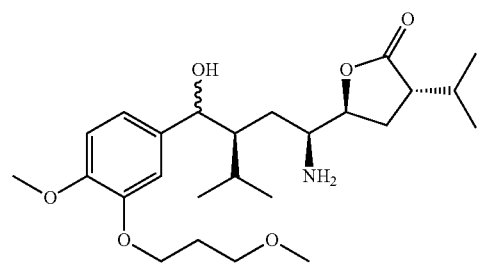

Formula VII-amine wherein Ar is substituted or unsubstituted aromatic aldehyde;

(b) deoxygenating by selectively reducing the compound of Formula VII-imine to obtain compound of the Formula VIIA-imine;

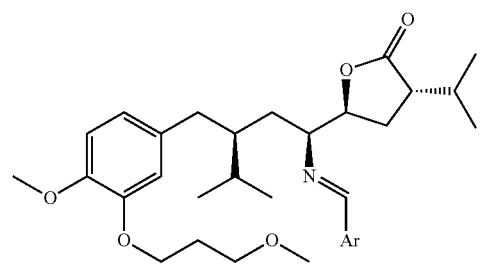

Formula VIIA-imine wherein Ar is substituted or unsubstituted aromatic aldehyde;

(c) deprotecting the compound of Formula VIIA-imine with inorganic or organic acid to obtain compound of Formula VIIA-amine;

Formula VIIA-amine

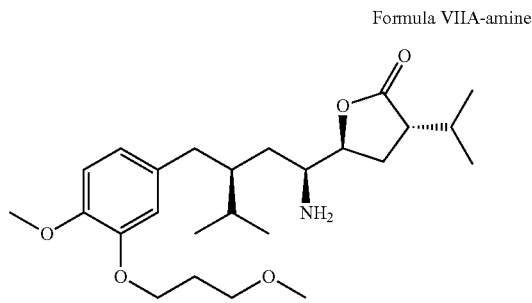 [SMILES: COCCCOc1cc(C[C@@H](C[C@H](N)[C@@H]2C[C@@H](C(C)C)C(=O)O2)C(C)C)ccc1OC]

(d) protecting the compound of Formula VIIA-amine with suitable protecting agent in presence of base to obtain compound of the Formula VIIA-N-PG;

Formula VIIA-N-PG

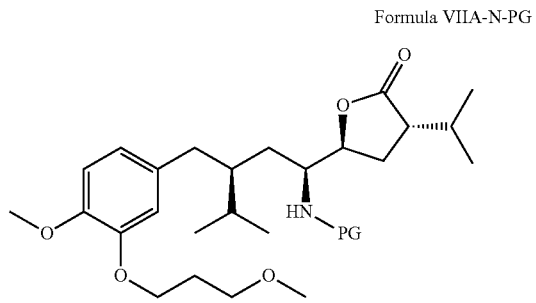

wherein PG is a protecting group selected from the group consisting of BOC, FMOC, substituted or unsubstituted Cbz and trityl;

(e) reacting the compound of Formula VIIA-N-PG with compound of Formula C in presence of 2-hydroxy pyridine and base to obtain compound of the Formula X—N-PG Formula C

H$_2$N—⟨⟩—NH$_2$ (O)

Formula X-N-PG

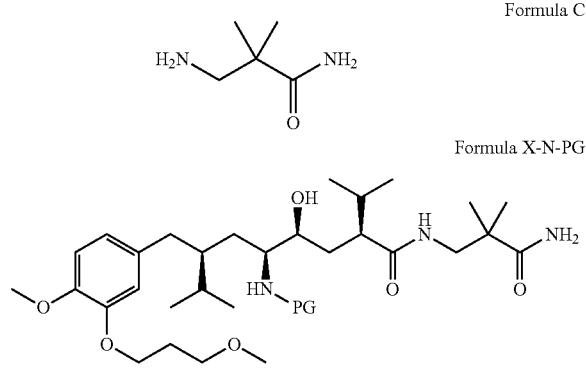

wherein PG is a protecting group selected from the group consisting of BOC, FMOC, substituted or unsubstituted Cbz and trityl;

(f) deprotecting the compound of Formula X—N-PG with acid or base or catalytic hydrogenolysis using hydrogen gas or catalytic hydrogen transfer in presence of organic solvent to obtain Aliskiren of the Formula X;

Formula X

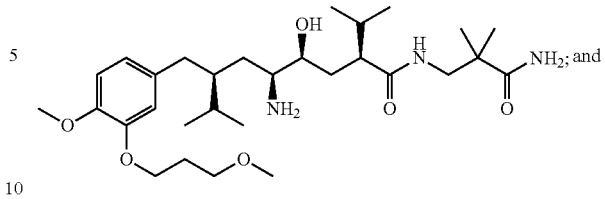

(g) treating Aliskiren of the Formula X with fumaric acid to obtain Aliskiren hemifumarate of Formula I.

17. The process according to claim 16, wherein reduction of the compound of Formula VII in step (a) is carried out in the presence of a metal catalyst in an organic solvent.

18. The process according to claim 17, wherein the metal catalyst is selected from the group consisting of Pd/C, Pt/C, PtO$_2$/C and Raney/Ni.

19. The process according to claim 17, wherein the organic solvent used in step (a) is selected from the group consisting of an alcohol selected from the group consisting of methanol, ethanol, propanol and butanol; an ester selected from the group consisting of ethyl acetate and isopropyl acetate; and methyl-tert-butyl ether.

20. The process according to claim 16, wherein conversion of the compound of Formula VII-imine to compound of Formula VII-amine is carried out with an acid in the presence of organic solvent.

21. The process according to claim 20, wherein the acid is selected from the group consisting of hydrofluoric acid, hydrochloric acid, hydrobromic acid, perchloric acid, phosphoric acid, acetic acid, citric acid and oxalic acid.

22. The process according to claim 20, wherein the organic solvent is selected from the group consisting of an alcohol selected from the group consisting of methanol, ethanol, propanol and butanol; an ester selected from the group consisting of ethyl acetate and isopropyl acetate; dichloromethane; and toluene.

23. The process according to claim 16, wherein reconversion of the compound of Formula VII-amine to compound of Formula VII-imine is carried out by reacting with substituted or unsubstituted aromatic aldehyde in an organic solvent.

24. The process according to claim 23, wherein the organic solvent is selected from the group consisting of an alcohol selected from the group consisting of methanol, ethanol, propanol and butanol; an ester selected from the group consisting of ethyl acetate and isopropyl acetate; dichloromethane; and toluene.

25. The process according to claim 16, wherein deoxygenation in step (b) is carried out in the presence of a trialkylsilane selected from the group consisting of triethylsilane (TES) in the presence of trimethylsilyl trifluoromethanesulfonate (TMSOTf), triethylsilane in trifluoroacetic acid; and triethylsilane in titanium tetrachloride.

26. The process according to claim 16, wherein deoxygenation in step (b) is carried out in the presence of an organic solvent selected from the group consisting of a chlorinated solvent selected from the group consisting of dichloromethane, dichloroethane and chloroform; an ether selected from the group consisting of THF and dioxane; and toluene.

27. The process according to claim 16, wherein the inorganic acid in step (c) is selected from the group consisting of hydrofluoric acid, hydrochloric acid, hydrobromic acid, perchloric acid and phosphoric acid.

28. The process according to claim 16, wherein the organic acid in step (c) is selected from the group consisting of acetic acid, citric acid and oxalic acid.

29. The process according to claim 16, wherein deprotection in step (c) is carried out in the presence of an organic solvent selected from the group consisting of an alcohol selected from the group consisting of methanol, ethanol and propanol; an ester selected from the group consisting of ethyl acetate and isopropyl acetate; an ether selected from the group consisting of methyl tert-butyl ether and diisopropyl ether; dichloromethane; and toluene.

30. The process according to claim 16, wherein the protecting agent in step (d) is selected from the group consisting of BOC anhydride, FMOC-Cl, substituted or unsubstituted CbzCl and trityl chloride.

31. The process according to claim 16, wherein the base used in step (d) is an inorganic base selected from the group consisting of sodium bicarbonate, sodium carbonate, potassium bicarbonate and potassium carbonate; or an organic base selected from the group consisting of triethylamine, diisopropylethylamine, tributylamine, dicyclohexylamine, piperidine and pyridine.

32. The process according to claim 16, wherein protection in step (d) is carried out in the presence of an organic solvent selected from the group consisting of a chlorinated solvent selected from the group consisting of dichloromethane, dichloroethane and chloroform; an ester selected from the group consisting of ethyl acetate and isopropyl acetate; and an ether selected from the group consisting of methyl-tert-butyl ether and tetrhydrofuran.

33. The process according to claim 16, wherein the reaction in step (e) is carried out optionally in the presence of the organic solvent selected from the group consisting of toluene and methyl tert-butyl ether.

34. The process according to claim 16, wherein the base in step (e) is selected from the group consisting of triethylamine, diisopropylethylamine and tributylamine.

35. The process according to claim 16, wherein acid used in step (f) is selected from the group consisting of an inorganic acid selected from hydrochloric acid, hydrogen bromide, hydrogen fluoride, hydrogen phosphate and perchloric acid and an organic acid selected from trifluoroacetic acid, para-toluene sulfonic acid, methanesulfonic acid and camphor sulfonic acid.

36. The process according to claim 16, wherein the base used in step (f) is selected from the group consisting of a metal alkoxide selected from the group consisting of sodium ethoxide, potassium ethoxide, sodium tert-butoxide and potassium tert-butoxide.

37. The process according to claim 16, wherein the organic solvent used in step (f) is selected from the group consisting of an ether selected from the group consisting of dioxane and tetrahydrofuran; a chlorinated solvent selected from the group consisting of dichloromethane, dichloroethane and chloroform; an ester selected from the group consisting of ethyl acetate and isopropyl acetate; and an alcohol selected from the group consisting of methanol, ethanol and propanol.

38. The process according to claim 16, wherein the reaction of step (g) is carried out in the presence of an organic solvent selected from the group consisting of an alcohol selected from the group consisting of methanol, ethanol and isopropanol; a nitrile selected from the group consisting of acetonitrile and propionitrile; an ester selected from the group consisting of ethyl acetate and isopropyl acetate; and a mixture thereof.

* * * * *